US 6,562,005 B1

(12) United States Patent
Donath

(10) Patent No.: US 6,562,005 B1
(45) Date of Patent: May 13, 2003

(54) CATHETER BUTTON SYSTEM AND SURGICAL METHOD OF ANCHORING CATHETER BUTTON

(76) Inventor: David Donath, 16 Applewood Road, Montreal, Quebec (CA), H3X 3W6

( * ) Notice: Subject to any disclaimer, the term of this patent is extended or adjusted under 35 U.S.C. 154(b) by 0 days.

(21) Appl. No.: 09/904,081

(22) Filed: Jul. 12, 2001

(30) Foreign Application Priority Data

May 2, 2001 (CA) .......................... 2,346,192

(51) Int. Cl.[7] .................. A61M 5/32; A61M 5/178; A61M 25/00; A61M 25/16; A61M 39/02

(52) U.S. Cl. .................. 604/174; 604/179; 604/164.04; 604/523; 604/533; 604/539

(58) Field of Search ................ 604/104, 174, 604/179, 180, 523, 533, 539, 164.04; 128/DIG. 6, DIG. 26

(56) References Cited

U.S. PATENT DOCUMENTS

| 3,176,690 A | | 4/1965 | H'Doubler | |
|---|---|---|---|---|
| 4,435,174 A | | 3/1984 | Redmond et al. | |
| 4,645,492 A | | 2/1987 | Weeks | |
| 4,834,713 A | | 5/1989 | Suthanthiran | |
| 5,320,629 A | * | 6/1994 | Noda et al. | 606/139 |
| 5,603,730 A | | 2/1997 | Romkee | |
| 5,616,131 A | | 4/1997 | Sauer et al. | |
| 5,741,234 A | | 4/1998 | Aboul-Hosn | |
| 5,891,168 A | | 4/1999 | Thal | |
| 6,143,017 A | * | 11/2000 | Thal | 606/232 |
| 6,200,330 B1 | * | 3/2001 | Benderev et al. | 606/232 |
| 6,299,895 B1 | * | 10/2001 | Hammang et al. | 424/427 |
| 6,344,056 B1 | * | 2/2002 | Dehdashtian | 623/1.35 |
| 6,416,781 B1 | * | 7/2002 | Vandamme | 424/438 |
| 2002/0120292 A1 | * | 8/2002 | Morgan | 606/232 |

* cited by examiner

Primary Examiner—Steven O. Douglas
Assistant Examiner—Anuradha Ramana
(74) Attorney, Agent, or Firm—Spencer Fane Britt & Browne LLP

(57) ABSTRACT

A catheter button system for anchoring a catheter to a patient's body tissue, consists of a catheter button having a primary aperture for snugly receiving a catheter tube, and at least one secondary aperture. A cord loop extends through the secondary aperture. The loop is for catching a surgeon's suture needle for fastening the button system to the patient's body tissue. Preferably, the button consists of separate upper and lower components, and the cord loop holds the button components together, as well as serving to anchor the button to a patient's body with a stitch of suture thread. Preferably, the primary aperture is central to the button, and two secondary apertures are spaced equidistant from the primary aperture, on opposing sides of the button. The invention also relates to a method for anchoring a suture to a patient's body, by joining a button to the suture, the button having at least one pre-formed loop. The button is then anchored to the patient's body, by passing a suture needle through the pre-made loop and stitching the loop to the body tissue.

9 Claims, 2 Drawing Sheets

CATHETER BUTTON SYSTEM AND SURGICAL METHOD OF ANCHORING CATHETER BUTTON

Priority benefit under 35 U. S. C. § 119 is claimed to Canadian Patent Application No. 2,346,192 filed May 2, 2001.

FIELD OF THE INVENTION

The present invention relates to catheter buttons for anchoring a catheter to tissue. The invention also relates to a method for anchoring a catheter to a patient's body, by fastening a catheter button to a patient's skin or other body tissue.

BACKGROUND OF THE INVENTION

Catheter buttons consist of small button-shaped devices, typically having a central aperture for receiving a catheter and anchoring means to anchor the button to body tissue. Typically, the anchoring means consist of a pair of apertures on either side of the button, through which a surgeon may suture the button directly onto the patient's skin or other tissue. A catheter is threaded through the central aperture for anchoring the catheter to the patient's body.

Typically, the button is in two parts, namely a disc-like member and a hemispherical member. The hemispherical member has a flat base and in use the disc portion abuts the flat base of the domed portion. The disc may comprise a radio opaque component, for use in radiological procedures. In use, the disc may abut the patient's body tissue with the domed portion projecting outwardly, or the structure may be inverted such that the domed portion abuts the patient's skin or other body tissue. For convenience, the disc portion will be referred to as the "lower" portion and the hemispherical member as the "upper" portion. An aligned central catheter-receiving aperture passes through both upper and lower portions, as do one, two or more aligned smaller apertures to the side of the button for receiving suture thread.

In use, both upper and lower components are joined to the catheter tube by sliding the catheter through the central aperture either before or after the catheter tube has been implanted within the patient's body. After the button has been snugged against the patient's body, the surgeon carefully loops a suture thread through the aligned side apertures and the patient's body, forming a thread loop which is then knotted to anchor the button and catheter in place. The process is relatively time consuming and painstaking, since several steps are required, each of which requires particular care.

Catheter buttons having this two part structure are disclosed in U.S. Pat. No. 4,834,713 (Suthanthiran). As well, such buttons are available commercially.

The primary disadvantages of the prior art system described above are the requirements that the surgeon must separately handle two small button components and that he must carefully direct a suture through the side apertures of the button, as well as the patient's body in order to anchor the button. Typically, the side apertures are relatively long and narrow, and passing a suture through these apertures is a painstaking, time consuming and finicky task which must of necessity occur in the surgical theatre where speed and accuracy are both important. There is also the necessity of separately supplying the two button components, adding to the cost and manpower requirements of performing a medical procedure.

SUMMARY AND OBJECTS OF THE INVENTION

It is an object of the present invention to provide an improved catheter button system which permits a surgeon to rapidly anchor a catheter to a patient's body. It is a further object to provide a method for surgically anchoring a catheter to a patient with a catheter button in a quick and convenient manner.

In one aspect, the invention comprises a catheter button system comprising a catheter button having a primary aperture for receiving a catheter tube and at least one and preferably at least two secondary apertures for receiving suture thread, with a pre-formed loop of cord or thread extending through the secondary apertures. The loop includes sufficient slack to permit a surgeon to catch the loop with a suture needle for stitching through a patient's skin or other tissue. The catheter button may comprise two separate components, the first component being disc-shaped and the second component, abutted against the first component, being generally hemispherical. The primary and secondary apertures extend through both components in an aligned fashion. In this embodiment, the cord loops extend through both components of the catheter button to retain them together. Conveniently, the cord loops comprise suture thread. Preferably, the primary aperture is centrally disposed and the secondary apertures comprise two apertures on opposing sides of the button, equispaced on either side of the primary aperture.

Catheter button systems of the present invention may encompass a variety of sizes and configurations for use with a range of catheter types and sizes and for use with a variety of surgical procedures or interventional radiologic procedures. The catheter button systems of the invention may comprise or consist of radio opaque or radiolucent components, depending on the intended use.

In a further aspect, the invention is a method for anchoring a suture to a patient's body, consisting of the steps of:
 providing a suture button, consisting of a primary aperture and at least one and preferably two or more secondary apertures, with a pre-formed cord loop extending through each of the secondary apertures;
 joining the button with a catheter by sliding the button onto the catheter through the primary aperture, either before or after an end of the catheter has been implanted within a patient's body;
 drawing the catheter button snugly against the patient's skin or tissue;
 anchoring the catheter button to the patient, by passing a suture thread through body tissue of a patient and catching the cord loop with the suture thread; and
 tying off the suture thread or otherwise fastening the cord loop to the suture thread in a snug fashion.

Preferably, two cord loops are provided on opposing sides of the button and the step of fastening the button to the patient's body tissue comprises separately suturing the two cord loops to the patient.

The invention also comprises a method for providing pre-made catheter button systems on-site at a medical facility. In this aspect, catheter button systems as characterized above are assembled on-site at a medical facility in advance of a surgical or other medical procedure. The button systems are then used in a procedure carried out at a subsequent time at the facility.

DETAILED DESCRIPTION OF THE PREFERRED EMBODIMENTS

Figure 1:
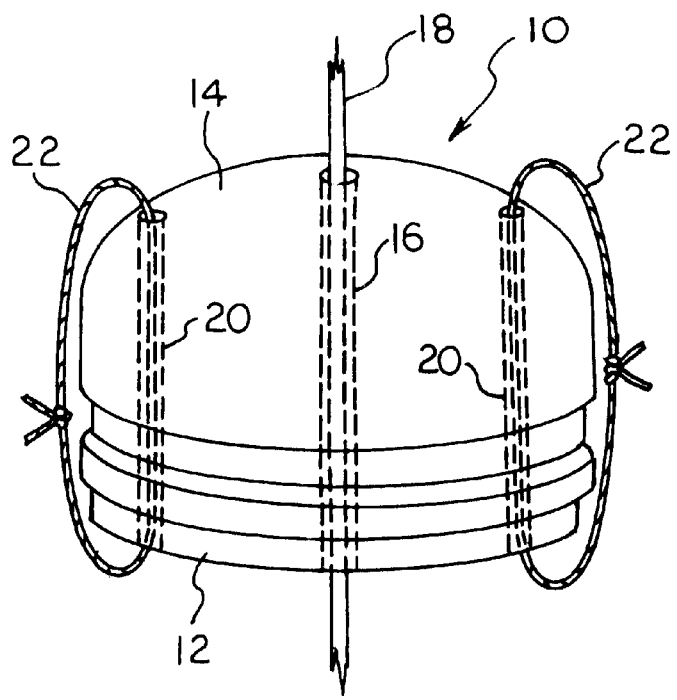
FIG. 1 is an isometric view of a catheter button according to the present invention.
Figure 2:
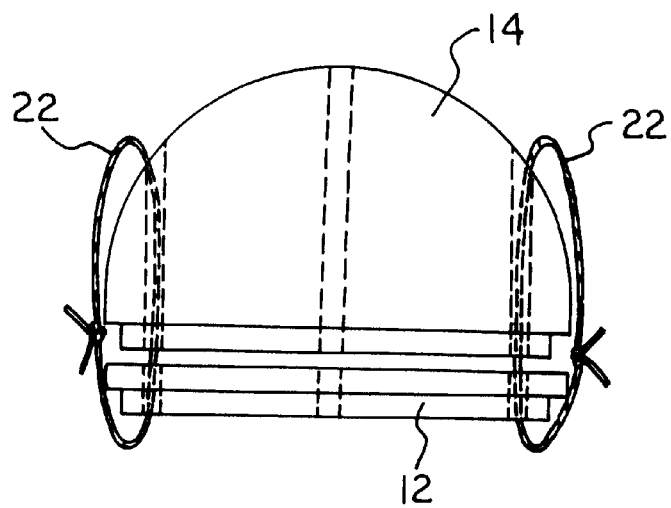
FIG. 2 is a side elevational view of a catheter button according to the invention.

FIGS. 1 and 2 illustrate a catheter button system according to the present invention. The button body 10 comprises two components. The first component is a disc portion 12, intended to abut the patient's body. The disc portion 12 may be either radiolucent or radio-opaque depending on the desired medical application. The second component is a generally hemispherical body portion 14, for abutting the disc portion 12. Both portions have an aligned central (primary) aperture 16, having a size suitable for snugly receiving a selected size of surgical catheter 18. As is known in the art, the catheter fits with sufficient snugness as to permit sliding of the button along the catheter, while gripping the catheter with a degree of friction to prevent unwanted movement of the catheter during and after the catheter anchoring procedure. The catheter button conventionally comprises rigid plastic. Conveniently, a variety of aperture and button sizes may be provided to accommodate various size catheters and surgical procedures.

On either side of the central aperture in both button components are a pair of side (secondary) apertures, aligned within the first and second button components, for receiving suture thread on opposed sides of the button. The side apertures are smaller in diameter than the central aperture.

While the preferred embodiment has two secondary apertures for anchoring the button to a patient, it will be seen that a button may be provided with additional apertures. Alternatively, systems may comprise a single secondary aperture and/or multiple primary apertures.

The catheter buttons of the invention are provided with a cord loop 22 extending through each of the side apertures 20. Conveniently, the loop may consist of a length of suture thread, which has been knotted to form a loop. Before the button has been installed on a catheter and anchored to a patient, the loops hold the two button components loosely together, as seen in FIG. 1. The loops each have a degree of slackness in them, sufficient to permit a surgeon to easily pass a suture needle through the loop for anchoring the button to a patient's body. For example, the secondary apertures 20 of the catheter button may each total about 5 mm. in length consisting of the sum of the lengths of the secondary apertures within the two button components, while the cord loops 22 may each have an extended length of about 12 to 15 mm., i.e. the length of the cord if the loop were to be severed and extended its full length for measurement purposes only.

Figure 3:
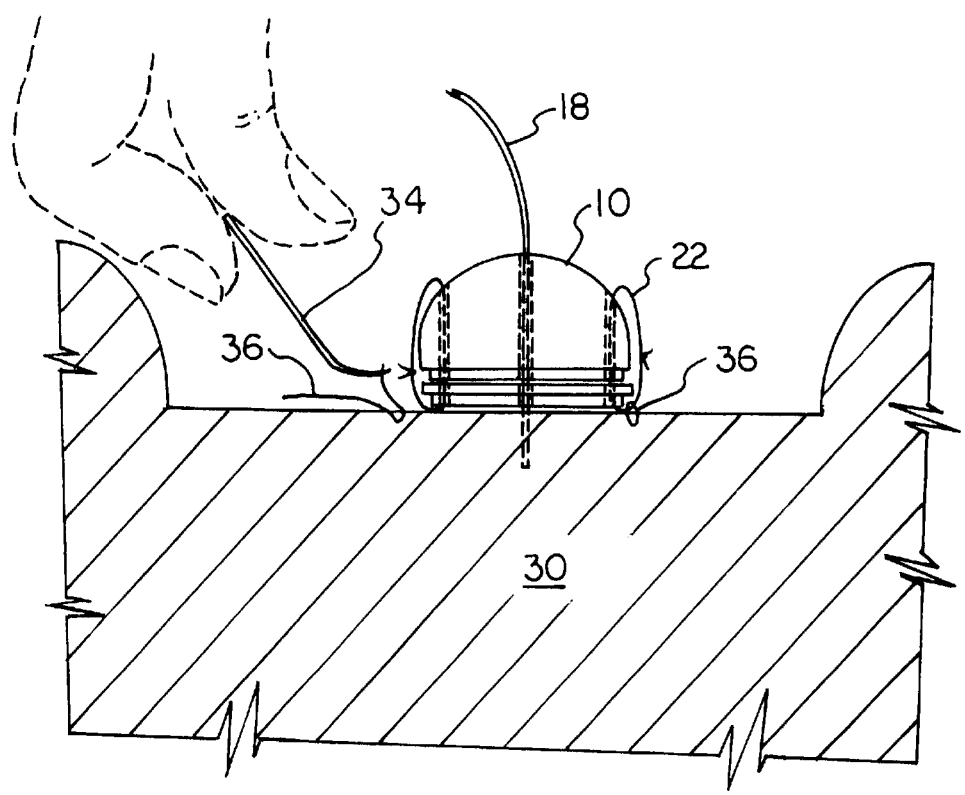
FIG. 3 is a partly schematic, isometric view of the catheter button, with a catheter engaged thereto, being anchored to a patient's body in a surgical operation.

FIG. 3 illustrates a typical method to anchor a catheter to a patient's body 30. A catheter button 10 as described above is joined onto a length of flexible surgical tubing 18 by sliding the button onto the tubing through the primary aperture 16. The suture button and tubing are size-matched wherein the tubing fits snugly within the central aperture of the catheter button such that it cannot freely slide within the aperture. The tubing or catheter 18 is then surgically implanted within a patient's body 30 in the desired location, in the course of a surgical or other procedure on a patient. The catheter button 10 is then slid along the catheter until it snugly abuts the appropriate portion of the patient's body, such as the patient's skin or other body tissue. Once in place, the surgeon anchors the catheter button, with catheter attached, to the patient's body by passing a suture needle 34, with suture thread 36 attached, through one of the cord loops 22 and through the body tissue. The surgeon then cuts off and knots the suture thread 36 or otherwise fastens the thread 36 and loop 22 together. The process is repeated on the other side of the button to catch the second loop with a suture passed through the patient's tissue.

The cord loops 22 on the catheter button are provided with sufficient slack to readily permit a surgeon to pass a catheter needle therethrough. However, the loops cannot have so much slack as to prevent the button from being snugly anchored against the patient's body.

It will be seen that the method for attaching a catheter button may be used in essentially any surgical operation or other medical procedure, such as a non-interventional radiological procedure, on any animal, human or otherwise. There is also no particular limitation on the size and configuration on the catheter button. Whilst the preferred embodiment comprises a two-part catheter button, it will be seen that the invention is not limited to this form of catheter button and may comprise a unitary button, or a multi-part button having more than two components.

In a further aspect of the invention, the cord loops 22 within the catheter button system may be formed at the hospital or other medical facility where the operation is to be carried out, in advance of the operation. Thus, a medical technician or other non-surgical personnel may in advance of the operation join together two components of a conventional catheter button, by passing a cord loop such as a length of suture thread, through each of the secondary apertures of the button. The loop is then knotted such that the cord loop has sufficient slack as described above. The ends of the suture thread are trimmed to a desirable length. The "preassembled" buttons may be then stored for future use at the medical facility. Conveniently, a number of button systems of different configurations, sizes and aperture sizes may be pre-formed and stockpiled The same method may be used to pre-assemble various types and configurations of catheter button systems as described above.

While the present invention has been described by way of preferred embodiments, it will be understood and appreciated by those skilled in the art to which this invention relates that various modifications may be made to the embodiments described above, including but not limited to the modification described above. Such modifications do not depart from the scope of the invention as defined in the appended claims.

I claim:

1. A catheter button system comprising a rigid body having a primary aperture therethrough for snugly receiving and retaining a catheter; at least two secondary apertures on either side of said primary aperture; and cord loops extending through said at least two secondary apertures, said loops each having sufficient slack to readily permit passage therethrough of a surgical suture needle and suture thread for snugly anchoring said button system and catheter to body tissue, said rigid body comprising separate upper and lower portions, held together by said cord loops.

2. A catheter button system as defined in claim 1, wherein said primary aperture comprises a single centrally disposed aperture and said secondary apertures comprise two apertures oppositely disposed on either side of said primary aperture.

3. A catheter button system as defined in claim 1, comprising more than two secondary apertures.

4. A catheter button system as defined in claim 1, wherein said primary aperture is centrally disposed.

5. A catheter button system as defined in claim 1, wherein said cord loops comprise suture thread.

6. A method for anchoring a catheter to a patient's body, comprising the steps of:

provides a catheter button system comprising a rigid body having a primary aperture and at least two secondary apertures, and a separate cord loop extending through each of said secondary apertures, said loops each having sufficient slack to permit passage therethrough of a surgical suture needle and suture thread, said rigid body comprising separate upper and lower components held together by said cord loops;

providing a length of catheter, having an outside diameter suitable for sliding through said primary aperture with sufficient friction to prevent the free movement thereof;

joining said catheter and button together by passing said catheter through said primary aperture;

implanting an end of said catheter within a patient's body either before or after engaging said button with said catheter;

drawing said catheter button along said catheter to rest snugly against patient's body; and passing a suture thread through said cord loops and through said patient's body tissue, and fastening said cord loops to said body tissue by separately knotting or otherwise fastening said thread to each of said cord loops.

7. A method as defined in claim 6, comprising the additional step of pre-assembling a multiplicity of said catheter button systems, on-site at a medical facility where the procedure of using said button systems is carried out.

8. A method as defined in claim 6, wherein said catheter button system comprises at least two equispaced secondary apertures, each having a cord loop passing therethrough and said step of passing a suture needle comprises passing a suture needle through each of said cord loops and separately fastening each of said cord loops to said body tissue.

9. A method for preparing a catheter button system in advance of a medical procedure, comprising:

providing a catheter button body having a primary aperture for snugly receiving a catheter and at least two secondary apertures each for receiving a cord loop;

on site at a medical facility, looping a separate cord loop through said at least two secondary apertures in advance of a surgical procedure at said facility, said loops including sufficient slack to permit catching said loops with a surgical suture; and storing said button system on site at said facility.

* * * * *